(12) United States Patent
Kamino et al.

(10) Patent No.: US 10,569,139 B2
(45) Date of Patent: Feb. 25, 2020

(54) GOLF BALL

(71) Applicant: DUNLOP SPORTS CO. LTD., Kobe-shi, Hyogo (JP)

(72) Inventors: Kazuya Kamino, Kobe (JP); Hidetaka Inoue, Kobe (JP); Toshiyuki Tarao, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 0 days.

(21) Appl. No.: 15/786,071

(22) Filed: Oct. 17, 2017

(65) Prior Publication Data

US 2018/0147451 A1    May 31, 2018

(30) Foreign Application Priority Data

Nov. 30, 2016   (JP) .................. 2016-232270

(51) Int. Cl.

| A63B 37/06 | (2006.01) |
|---|---|
| A63B 37/00 | (2006.01) |
| A63B 47/00 | (2006.01) |
| B32B 25/08 | (2006.01) |
| B32B 25/16 | (2006.01) |
| C08J 7/04 | (2020.01) |
| G01N 3/42 | (2006.01) |

(52) U.S. Cl.
CPC ........ *A63B 37/0022* (2013.01); *A63B 37/008* (2013.01); *A63B 37/0012* (2013.01); *A63B 37/0019* (2013.01); *A63B 37/0031* (2013.01); *A63B 37/0033* (2013.01); *A63B 37/0043* (2013.01); *A63B 37/0045* (2013.01); *A63B 37/0064* (2013.01); *A63B 37/0073* (2013.01); *A63B 37/0074* (2013.01); *A63B 37/0075* (2013.01); *A63B 47/008* (2013.01); *B32B 25/08* (2013.01); *B32B 25/16* (2013.01); *C08J 7/047* (2013.01); *G01N 3/42* (2013.01); *A63B 37/0076* (2013.01); *B32B 2307/536* (2013.01); *C08J 2323/08* (2013.01); *C08J 2351/04* (2013.01); *C08J 2475/08* (2013.01)

(58) Field of Classification Search
CPC ....................... A63B 37/0023; A63B 37/0022
USPC ......................................................... 473/371
See application file for complete search history.

(56) References Cited

U.S. PATENT DOCUMENTS

| 9,168,423 | B2 * | 10/2015 | Tarao | ............. A63B 37/0023 |
| 2011/0053708 | A1 * | 3/2011 | Isoagawa | ........... A63B 37/0022 |
| | | | | 473/376 |
| 2011/0244989 | A1 | 10/2011 | Tarao et al. | |
| 2013/0157782 | A1 | 6/2013 | Komatsu et al. | |
| 2013/0157783 | A1 | 6/2013 | Komatsu et al. | |

(Continued)

*Primary Examiner* — Raeann Gorden
(74) *Attorney, Agent, or Firm* — Birch, Stewart, Kolasch & Birch, LLP

(57) ABSTRACT

A golf ball 2 includes a main body 4 and a paint layer 6 positioned outside the main body 4. The main body 4 includes a spherical core 8, a mid layer 10 positioned outside the core 8, and a cover 12 positioned outside the mid layer 10. An indentation depth, measured when the paint layer 6 in a cross-section along a plane passing through a central point of the golf ball 2 is pressed by a force of 30 mgf in a direction perpendicular to the cross-section, is not less than 300 nm and not greater than 3000 nm. The paint layer 6 preferably has a thickness of not less than 5 μm and not greater than 50 μm.

12 Claims, 2 Drawing Sheets

(56) References Cited

U.S. PATENT DOCUMENTS

| | | |
|---|---|---|
| 2013/0157784 A1 | 6/2013 | Komatsu et al. |
| 2013/0331205 A1 | 12/2013 | Tarao et al. |
| 2015/0273276 A1* | 10/2015 | Isogawa .................. C08G 18/10 473/374 |
| 2016/0184654 A1 | 6/2016 | Matsuyama et al. |

* cited by examiner

GOLF BALL

This application claims priority on Patent Application No. 2016-232270 filed in JAPAN on Nov. 30, 2016. The entire contents of this Japanese Patent Application are hereby incorporated by reference.

BACKGROUND OF THE INVENTION

Field of the Invention

The present invention relates to golf balls. Specifically, the present invention relates to golf balls having a paint layer on the surface thereof.

Description of the Related Art

When a golf ball is hit with a golf club, the golf ball flies with backspin. When the rate of the backspin is high, the run of the golf ball after landing is short. By using a golf ball having a high backspin rate, a golf player can cause the golf ball to stop at a target point. When the rate of sidespin is high, the golf ball tends to curve. By using a golf ball having a high sidespin rate, a golf player can intentionally cause the golf ball to curve. For golf players, the spin performance of golf balls is important.

Golf players place importance on feel at impact of golf balls as well as spin performance. Golf players prefer soft feel at impact.

Most golf balls have a paint layer on the surface thereof. The roles of the paint layer are to enhance the appearance of golf balls and prevent staining of golf balls. Furthermore, the paint layer can also contribute to spin performance and feel at impact.

JP2011-217820 (US2011/0244989 A1) discloses a golf ball including a paint layer having a predetermined Martens hardness and a predetermined modulus. The golf ball has excellent spin performance in a wet state.

JP2013-126541 (US2013/0157782 A1) discloses a golf ball including a paint layer having a predetermined Young's modulus. The golf ball has excellent spin performance. JP2013-126542 (US2013/0157782 A1 and US2013/0157784 A1) and JP2013-126543 (US2013/0157782 A1 and US2013/0157783 A1) also disclose similar golf balls.

JP2014-14383 (US2013/0331205 A1) discloses a golf ball including a paint layer having a predetermined storage modulus and a predetermined loss tangent. The golf ball has excellent spin performance upon an approach shot.

JP2016-123632 (US2016/0184654 A1) discloses a golf ball including a paint layer having a predetermined elastic modulus. The golf ball has excellent stain resistance.

Since the paint layer is thin, it is difficult to directly measure the physical properties of the paint layer. The Martens hardness and the modulus disclosed in JP2011-217820 (US2011/0244989 A1) are measured on a slab having the same composition as the composition of the paint layer. Therefore, the measurement results do not accurately reflect behavior of the paint layer in the golf ball. The spin performance of the golf ball disclosed in JP2011-217820 is not sufficient.

The Young's modulus disclosed in JP2013-126541 (US2013/0157782 A1) is measured on a sheet having a thickness of 2 mm. Therefore, the measurement results do not accurately reflect behavior of the paint layer in the golf ball. The spin performance of the golf ball disclosed in JP2013-126541 is not sufficient. The spin performance of the golf balls disclosed in JP2013-126542 (US2013/0157782 A1 and US2013/0157784 A1) and JP2013-126543 (US2013/0157782 A1 and US2013/0157783 A1) is also not sufficient.

The storage modulus and the loss tangent disclosed in JP2014-14383 (US2013/0331205 A1) are measured on a film having the same composition as the composition of the paint layer. Therefore, the measurement results do not accurately reflect behavior of the paint layer in the golf ball. The spin performance of the golf ball disclosed in JP2014-14383 is not sufficient.

The elastic modulus disclosed in JP2016-123632 (US2016/0184654 A1) is measured with a scanning probe microscope. Therefore, the measurement results are influenced by the physical properties of a cover under the paint layer. The spin performance of the golf ball disclosed in JP2016-123632 is not sufficient.

An object of the present invention is to provide a golf ball having excellent spin performance, excellent feel at impact, and excellent stain resistance. Another object of the present invention is to provide an evaluation method by which a true physical property of a paint layer can be measured.

SUMMARY OF THE INVENTION

A golf ball according to the present invention includes a main body and a paint layer positioned outside the main body. An indentation depth, measured when the paint layer in a cross-section along a plane passing through a central point of the golf ball is pressed in a direction perpendicular to the cross-section, is not less than 300 nm and not greater than 3000 nm.

The golf ball according to the present invention has excellent spin performance, excellent feel at impact, and excellent stain resistance.

Preferably, the indentation depth is not less than 400 nm and not greater than 3000 nm.

Preferably, the paint layer has a thickness of not less than 5 μm and not greater than 50 μm.

The main body may include a core and a cover positioned outside the core. The paint layer is laminated on the cover. Preferably, the cover has a Shore D hardness of not less than 20 and not greater than 50, and the indentation depth is not less than 400 nm and not greater than 3000 nm. The cover may have a Shore D hardness of not less than 50 and not greater than 80, and the indentation depth may be not less than 300 nm and not greater than 2500 nm.

A golf ball evaluation method according to the present invention includes the steps of:

cutting a golf ball including a paint layer; and pressing a cross-section of the paint layer exposed as a result of the cutting and measuring an indentation depth of the paint layer.

By the evaluation method according to the present invention, a physical property of the paint layer of the golf ball can be objectively evaluated.

DESCRIPTION OF THE PREFERRED EMBODIMENTS

The following will describe in detail the present invention based on preferred embodiments with appropriate reference to the drawings.

First Embodiment

Figure 1:
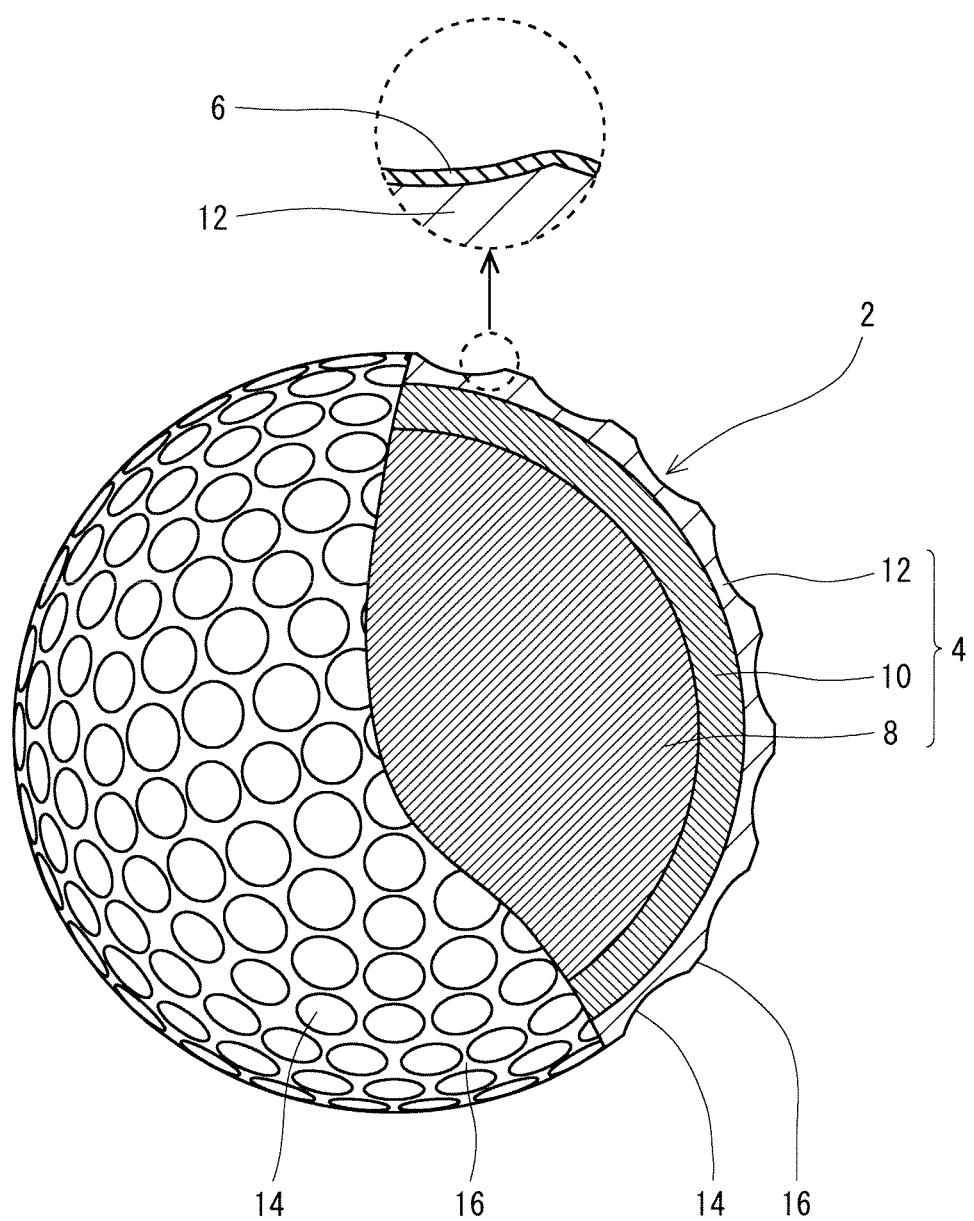
FIG. 1 is a partially cutaway cross-sectional view of a golf ball according to one embodiment of the present invention.

A golf ball 2 shown in FIG. 1 includes a main body 4 and a paint layer 6 positioned outside the main body 4. The main body 4 includes a spherical core 8, a mid layer 10 positioned outside the core 8, and a cover 12 positioned outside the mid layer 10. The golf ball 2 has a so-called three-piece structure. The golf ball 2 has a plurality of dimples 14 on the surface thereof. Of the surface of the golf ball 2, a part other than the dimples 14 is a land 16. The golf ball 2 may include a mark layer. The mark layer may be positioned between the cover 12 and the paint layer 6, or may be positioned outside the paint layer 6.

The golf ball 2 preferably has a diameter of not less than 40 mm and not greater than 45 mm. From the viewpoint of conformity to the rules established by the United States Golf Association (USGA), the diameter is particularly preferably not less than 42.67 mm. In light of suppression of air resistance, the diameter is more preferably not greater than 44 mm and particularly preferably not greater than 42.80 mm. The golf ball 2 preferably has a weight of not less than 40 g and not greater than 50 g. In light of attainment of great inertia, the weight is more preferably not less than 44 g and particularly preferably not less than 45.00 g. From the viewpoint of conformity to the rules established by the USGA, the weight is particularly preferably not greater than 45.93 g.

The core 8 is formed by crosslinking a rubber composition. Examples of the base rubber of the rubber composition include polybutadienes, polyisoprenes, styrene-butadiene copolymers, ethylene-propylene-diene copolymers, and natural rubbers. Two or more rubbers may be used in combination. In light of resilience performance, polybutadienes are preferable, and high-cis polybutadienes are particularly preferable.

The rubber composition of the core 8 includes a co-crosslinking agent. Examples of preferable co-crosslinking agents in light of resilience performance include zinc acrylate, magnesium acrylate, zinc methacrylate, and magnesium methacrylate. The rubber composition preferably includes an organic peroxide together with a co-crosslinking agent. Examples of preferable organic peroxides include dicumyl peroxide, 1,1-bis(t-butylperoxy)-3,3,5-trimethylcyclohexane, 2,5-dimethyl-2,5-di(t-butylperoxy)hexane, and di-t-butyl peroxide.

The rubber composition of the core 8 may include additives such as a filler, sulfur, a vulcanization accelerator, a sulfur compound, an anti-aging agent, a coloring agent, a plasticizer, and a dispersant. The rubber composition may include a carboxylic acid or a carboxylate. The rubber composition may include synthetic resin powder or cross-linked rubber powder.

The core 8 has a diameter of preferably not less than 30.0 mm and particularly preferably not less than 38.0 mm. The diameter of the core 8 is preferably not greater than 42.0 mm and particularly preferably not greater than 41.5 mm. The core 8 may include two or more layers. The core 8 may have a rib on the surface thereof. The core 8 may be hollow.

The mid layer 10 is formed from a resin composition. A preferable base polymer of the resin composition is an ionomer resin. Examples of preferable ionomer resins include binary copolymers formed with an $\alpha$-olefin and an $\alpha, \beta$-unsaturated carboxylic acid having 3 to 8 carbon atoms. Examples of other preferable ionomer resins include ternary copolymers formed with: an $\alpha$-olefin; an $\alpha, \beta$-unsaturated carboxylic acid having 3 to 8 carbon atoms; and an $\alpha, \beta$-unsaturated carboxylate ester having 2 to 22 carbon atoms. For the binary copolymer and the ternary copolymer, preferable $\alpha$-olefins are ethylene and propylene, while preferable $\alpha, \beta$-unsaturated carboxylic acids are acrylic acid and methacrylic acid. In the binary copolymer and the ternary copolymer, some of the carboxyl groups are neutralized with metal ions. Examples of metal ions for use in neutralization include sodium ion, potassium ion, lithium ion, zinc ion, calcium ion, magnesium ion, aluminum ion, and neodymium ion.

Instead of an ionomer resin or together with an ionomer resin, the resin composition of the mid layer 10 may include another polymer. Examples of the other polymer include polystyrenes, polyamides, polyesters, polyolefins, and polyurethanes. The resin composition may include two or more polymers.

The resin composition of the mid layer 10 may include a coloring agent such as titanium dioxide, a filler such as barium sulfate, a dispersant, an antioxidant, an ultraviolet absorber, a light stabilizer, a fluorescent material, a fluorescent brightener, and the like. For the purpose of adjusting specific gravity, the resin composition may include powder of a metal with a high specific gravity such as tungsten, molybdenum, and the like.

The mid layer 10 has a Shore D hardness of preferably not less than 40 and particularly preferably not less than 50. The Shore D hardness of the mid layer 10 is preferably not greater than 80 and particularly preferably not greater than 70. The mid layer 10 has a thickness of preferably not less than 0.2 mm and particularly preferably not less than 0.3 mm. The thickness of the mid layer 10 is preferably not greater than 2.5 mm and particularly preferably not greater than 2.2 mm. The mid layer 10 has a specific gravity of preferably not less than 0.90 and particularly preferably not less than 0.95. The specific gravity of the mid layer 10 is preferably not greater than 1.10 and particularly preferably not greater than 1.05. The mid layer 10 may include two or more layers.

The cover 12 is formed from a resin composition. A preferable base polymer of the resin composition is a polyurethane. The resin composition may include a thermoplastic polyurethane or may include a thermosetting polyurethane. In light of productivity, the thermoplastic polyurethane is preferable. The thermoplastic polyurethane includes a polyurethane component as a hard segment, and a polyester component or a polyether component as a soft segment. The cover 12 the base material of which is the polyurethane can contribute to the spin performance of the golf ball 2. Furthermore, the cover 12 can also contribute to the feel at impact of the golf ball 2.

The polyurethane has a urethane bond within the molecule. The urethane bond can be formed by reacting a polyol with a polyisocyanate.

The polyol, which is a material for the urethane bond, has a plurality of hydroxyl groups. Low-molecular-weight polyols and high-molecular-weight polyols can be used.

Examples of an isocyanate for the polyurethane component include alicyclic diisocyanates, aromatic diisocyanates, and aliphatic diisocyanates. Alicyclic diisocyanates are particularly preferable. Since an alicyclic diisocyanate does not have any double bond in the main chain, the alicyclic diisocyanate suppresses yellowing of the cover 12. Examples of alicyclic diisocyanates include 4,4'-dicyclohexylmethane diisocyanate ($H_{12}$MDI), 1,3-bis(isocyanatomethyl)cyclohexane ($H_6$XDI), isophorone diisocyanate (IPDI), and trans-1,4-cyclohexane diisocyanate (CHDI). In light of versatility and processability, $H_{12}$MDI is preferable.

Instead of a polyurethane, the resin composition of the cover 12 may include another polymer. Examples of the other polymer include ionomer resins, polystyrenes, polyamides, polyesters, and polyolefins. The resin composition may include two or more polymers.

The resin composition of the cover 12 may include a coloring agent such as titanium dioxide, a filler such as barium sulfate, a dispersant, an antioxidant, an ultraviolet absorber, a light stabilizer, a fluorescent material, a fluorescent brightener, and the like.

The cover 12 preferably has a hardness Hc of not less than 20 and not greater than 50. The cover 12 having a hardness Hc of not less than 20 has excellent durability. From this viewpoint, the hardness Hc is more preferably not less than 22 and particularly preferably not less than 24. The golf ball 2 including the cover 12 having a hardness Hc of not greater than 50 has excellent spin performance. From this viewpoint, the hardness Hc is more preferably not greater than 48 and particularly preferably not greater than 46.

The hardness of the cover 12 (or the mid layer 10) is measured according to the standards of "ASTM-D 2240-68". The hardness is measured with a Shore D type hardness scale mounted to an automated hardness meter (trade name "digi test II" manufactured by Heinrich Bareiss Prüfgerätebau GmbH). For the measurement, a sheet that is formed by hot press, is formed from the same material as that of the cover 12 (or the mid layer 10), and has a thickness of about 2 mm is used. Prior to the measurement, a sheet is kept at 23° C. for two weeks. At the measurement, three sheets are stacked.

In light of spin performance, the cover 12 has a thickness of preferably not less than 0.1 mm, more preferably not less than 0.3 mm, and particularly preferably not less than 0.4 mm. In light of flight performance of the golf ball 2, this thickness is preferably not greater than 2.0 mm, more preferably not greater than 1.5 mm, and particularly preferably not greater than 1.0 mm. The thickness is measured at a position immediately below the land 16.

The cover 12 may include two or more layers.

The golf ball 2 may include a reinforcing layer between the mid layer 10 and the cover 12. The reinforcing layer firmly adheres to the mid layer 10 and also to the cover 12. The reinforcing layer suppresses separation of the cover 12 from the mid layer 10. The reinforcing layer is formed from a polymer composition. Examples of the base polymer of the reinforcing layer include two-component curing type epoxy resins and two-component curing type urethane resins.

The paint layer 6 is laminated on the cover 12. The paint layer 6 is formed from a resin composition. Examples of the base material of the resin composition include polyurethanes, epoxy resins, acrylic resins, polyvinyl acetate resins, and polyesters. Particularly preferable base resins are polyurethanes. Polyurethanes can contribute to the spin performance of the golf ball 2.

Typically, the paint layer 6 is formed from a polyurethane paint. The paint contains a polyol composition and a polyisocyanate composition. In the paint, a polyol is a base material, and a polyisocyanate is a curing agent.

The polyol composition contains a polyol compound. The polyol compound has two or more hydroxyl groups within the molecule thereof. The polyol compound may have a hydroxyl group at an end of the molecule thereof, or may have a hydroxyl group at the portion of the molecule other than the ends thereof. The polyol composition may contain two or more polyol compounds.

The polyol compound having a hydroxyl group at an end of the molecule thereof includes a low-molecular-weight polyol and a high-molecular-weight polyol.

Examples of the low-molecular-weight polyol include: diols such as ethylene glycol, diethylene glycol, triethylene glycol, 1,3-butanediol, 1,4-butanediol, neopentyl glycol, and 1,6-hexanediol; and triols such as glycerin, trimethylol propane, and hexanetriol.

Examples of the high-molecular-weight polyol include: polyether polyols, polyester polyols, polycaprolactone polyols, polycarbonate polyols, urethane polyols, and acrylic polyols. Examples of polyether polyols include polyoxyethylene glycol (PEG), polyoxypropylene glycol (PPG), and polyoxytetramethylene glycol (PTMG). Examples of polyester polyols include polyethylene adipate (PEA), polybutylene adipate (PBA), and polyhexamethylene adipate (PHMA). Examples of polycaprolactone polyols include poly-ε-caprolactone (PCL). Examples of polycarbonate polyols include polyhexamethylene carbonate.

From the viewpoint that the curing time of the paint is short, a preferable polyol compound is a urethane polyol. The urethane polyol has two or more urethane bonds and two or more hydroxyl groups. The urethane polyol can be obtained by causing a reaction of a polyol component and a polyisocyanate component under a condition that the hydroxyl groups of the polyol component are excessive with respect to the isocyanate groups of the polyisocyanate component.

Examples of the polyol component, which is a starting material of the urethane polyol, include polyether diols, polyester diols, polycaprolactone diols, and polycarbonate diols. A preferable polyol component is a polyether diol. Examples of the polyether diol include polyoxyethylene glycol, polyoxypropylene glycol, and polyoxytetramethylene glycol. A preferable polyether diol is polyoxytetramethylene glycol.

The polyether diol preferably has a number average molecular weight of not less than 550. The polyether diol having a number average molecular weight of not less than 550 can contribute to spin performance. From this viewpoint, this molecular weight is more preferably not less than 600 and particularly preferably not less than 630. The molecular weight is preferably not greater than 3000. The polyether diol having a molecular weight of not greater than 3000 can contribute to the stain resistance of the paint layer 6. From this viewpoint, the molecular weight is more preferably not greater than 2500 and particularly preferably not greater than 2000. The number average molecular weight of the polyol component is measured by gel permeation chromatography (GPC). The measurement conditions are as follows.

Reference material: polystyrene

Eluant: tetrahydrofuran

Column: organic solvent GPC column ("Shodex KF Series" manufactured by Showa Denko K.K.)

The content of the polyether diol in the urethane polyol is preferably not less than 60% by weight. The urethane polyol the content of which is not less than 60% by weight can contribute to spin performance. From this viewpoint, this content is more preferably not less than 62% by weight and particularly preferably not less than 65% by weight.

A low-molecular-weight polyol can be used as the polyol component, which is the starting material of the urethane polyol. Examples of the low-molecular-weight polyol include: diols such as ethylene glycol, diethylene glycol, triethylene glycol, 1,3-butanediol, 1,4-butanediol, neopentyl glycol, and 1,6-hexanediol; and triols such as glycerin, trimethylol propane, and hexanetriol. Two or more low-molecular-weight polyols may be used as the starting material.

The polyisocyanate component, which is a starting material of the urethane polyol, has two or more isocyanate groups. Examples of the polyisocyanate component include: aromatic polyisocyanates such as 2,4-toluene diisocyanate, 2,6-toluene diisocyanate, a mixture (TDI) of 2,4-toluene diisocyanate and 2,6-toluene diisocyanate, 4,4'-diphenylmethane diisocyanate (MDI), 1,5-naphthylene diisocyanate (NDI), 3,3'-bitolylene-4,4'-diisocyanate (TODI), xylylene diisocyanate (XDI), tetramethylxylylene diisocyanate (TMXDI), and paraphenylene diisocyanate (PPDI); alicyclic polyisocyanates such as 4,4'-dicyclohexylmethane diisocyanate ($H_{12}$MDI), hydrogenated xylylene diisocyanate ($H_6$XDI), hexamethylene diisocyanate (HDI), isophorone diisocyanate (IPDI), and norbornene diisocyanate (NBDI); and aliphatic diisocyanates. As the starting material, two or more polyisocyanates may be used.

The urethane polyol preferably has a weight average molecular weight of not less than 4000. The urethane polyol having a weight average molecular weight of not less than 4000 can contribute to spin performance. From this viewpoint, the molecular weight is more preferably not less than 4300 and particularly preferably not less than 4500. The molecular weight is preferably not greater than 20000. The urethane polyol having a molecular weight of not greater than 20000 can contribute to the stain resistance of the paint layer 6. From this viewpoint, this molecular weight is more preferably not greater than 18000 and particularly preferably not greater than 16000.

The urethane polyol has a hydroxyl value of preferably not less than 10 mg KOH/g, more preferably not less than 15 mg KOH/g, and particularly preferably not less than 20 mg KOH/g. The hydroxyl value is preferably not greater than 200 mg KOH/g, more preferably not greater than 190 mg KOH/g, and particularly preferably not greater than 180 mg KOH/g. The hydroxyl value is measured according to the standards of "JIS K 1557-1". For the measurement, the acetylation method is adopted.

The polyisocyanate composition that is a curing agent liquid in the paint contains a polyisocyanate compound. The polyisocyanate compound has two or more isocyanate groups.

Examples of the polyisocyanate compound include: aromatic diisocyanates such as 2,4-toluene diisocyanate, 2,6-toluene diisocyanate, a mixture (TDI) of 2,4-toluene diisocyanate and 2,6-toluene diisocyanate, 4,4'-diphenylmethane diisocyanate (MDI), 1,5-naphthylene diisocyanate (NDI), 3,3'-bitolylene-4,4'-diisocyanate (TODI), xylylene diisocyanate (XDI), tetramethylxylylene diisocyanate (TMXDI), and paraphenylene diisocyanate (PPDI); alicyclic or aliphatic diisocyanates such as 4,4'-dicyclohexylmethane diisocyanate ($H_{12}$MDI), hydrogenated xylylene diisocyanate ($H_6$XDI), hexamethylene diisocyanate (HDI), isophorone diisocyanate (IPDI), and norbornene diisocyanate (NBDI); and triisocyanates such as an allophanate product, a biuret product, an isocyanurate product, an adduct product of diisocyanates. The polyisocyanate compound may include two or more isocyanates.

Examples of preferable triisocyanates include an isocyanurate product of hexamethylene diisocyanate, a biuret product of hexamethylene diisocyanate, and an isocyanurate product of isophorone diisocyanate.

Preferably, the polyisocyanate composition contains a triisocyanate compound. The proportion of the triisocyanate compound to the entire polyisocyanate in the polyisocyanate composition is preferably not less than 50% by weight, more preferably not less than 60% by weight, and particularly preferably not less than 70% by weight. The polyisocyanate composition may contain only the triisocyanate compound as the polyisocyanate compound.

The isocyanate group amount (NCO %) of the polyisocyanate contained in the polyisocyanate composition is preferably not less than 0.5% by weight, more preferably not less than 1.0% by weight, and particularly preferably not less than 2.0% by weight. The isocyanate group amount is preferably not greater than 45% by weight, more preferably not greater than 40% by weight, and particularly preferably not greater than 35% by weight. The isocyanate group amount (NCO %) is calculated by the following mathematical formula.

$$NCO=(100 \times Mi \times 42)/Wi$$

Mi: the number of moles of the isocyanate groups in the polyisocyanate
42: the molecular weight of NCO
Wi: the total weight (g) of the polyisocyanate Specific examples of the polyisocyanate include: trade names "BURNOCK D-800", "BURNOCK DN-950", "BURNOCK DN-955", manufactured by DIC corporation; trade names "Desmodur N 75 MPA/X", "Desmodur N 3300", "Desmodur L 75 (C)", "Desmodur Z 4470", and "Sumidur E21-1", manufactured by Sumika Bayer Urethane CO., Ltd.; trade names "CORONATE HX" and "CORONATE HK", manufactured by Tosoh Corporation; trade names "DURANATE 24A-100", "DURANATE 21S-75E", "DURANATE TPA-100", and "DURANATE TKA-100", manufactured by Asahi Kasei Chemicals Corporation; and trade name "VESTANAT T1890" manufactured by Degussa AG.

The mole ratio (NCO group/OH group) of the hydroxyl group (OH group) of the base material and the isocyanate group (NCO group) of the curing agent in the curing type paint composition is preferably not less than 0.1. The paint layer 6 having excellent stain resistance can be formed from the composition in which the mole ratio (NCO group/OH group) is not less than 0.1. From this viewpoint, the mole ratio is particularly preferably not less than 0.2. The mole ratio is preferably not greater than 2.0. The composition in which the mole ratio is not greater than 2.0 can contribute to the spin performance of the golf ball 2. From this viewpoint, the ratio is more preferably not greater than 1.8 and particularly preferably not greater than 1.6.

The paint layer 6 can be formed by applying the paint onto the surface of the main body 4. The paint may be applied in an overlapped manner. In the case of application in an overlapped manner, the paint applied earlier and the paint applied later may be of the same type or may be of different types.

The paint layer 6 preferably has a thickness Tp of not less than 5 μm and not greater than 50 μm. The paint layer 6 having a thickness Tp of not less than 5 μm can contribute to spin performance. From this viewpoint, the thickness Tp is more preferably not less than 6 μm and particularly preferably not less than 7 μm. The paint layer 6 having a thickness Tp of not greater than 50 μm has excellent durability. From this viewpoint, the thickness Tp is more preferably not greater than 40 μm and particularly preferably not greater than 30 µm. In the case where the paint is applied in an overlapped manner, the total thickness of a plurality of layers only needs to fall within the above range.

The paint layer 6 preferably has an indentation depth of not less than 300 nm and not greater than 3000 nm. The paint layer 6 having an indentation depth of not less than 300 nm can contribute to spin performance. From this viewpoint, the indentation depth is more preferably not less than 400 nm and particularly preferably not less than 500 nm. The paint layer 6 having an indentation depth of not greater than 3000 nm has excellent stain resistance. From this viewpoint, the indentation depth is more preferably not greater than 2500 nm and particularly preferably not greater than 2000 nm.

In measurement of the indentation depth, the golf ball 2 is divided to obtain a hemisphere. On the hemisphere, a cross-section passing through the central point of the golf ball 2 is exposed. The cross-section includes a cross-section of the paint layer 6. The cross-section of the hemisphere is made horizontal by a cryo-microtome. A penetrator of a nanoindenter is brought into contact with the paint layer 6 in this cross-section and pressed against the paint layer 6 in a direction perpendicular to the cross-section. Due to this pressing, the penetrator advances. A load and an advancing distance of the penetrator are measured. The conditions at the measurement are as follows.

Nanoindenter: "ENT-2100" manufactured by ELIONIX INC.

Temperature: 30° C.

Penetrator: a Berkovich penetrator (65.03° As (h)=26.43 $h^2$)

Number of partitions: 500 steps

Step interval: 20 msec (100 mgf)

The load of the penetrator is gradually increased until reaching 50 mgf. The advancing distance of the penetrator is measured when the load is 30 mgf.

By the measurement of the indentation depth, the hardness of the paint layer 6 can be evaluated without influence of the hardness of the cover 12. The evaluation method according to the present invention includes the steps of:

(1) cutting the golf ball 2 including the paint layer 6; and (2) pressing a cross-section of the paint layer 6 exposed as a result of the above cutting and measuring an indentation depth of the paint layer 6.

Second Embodiment

Figure 2:
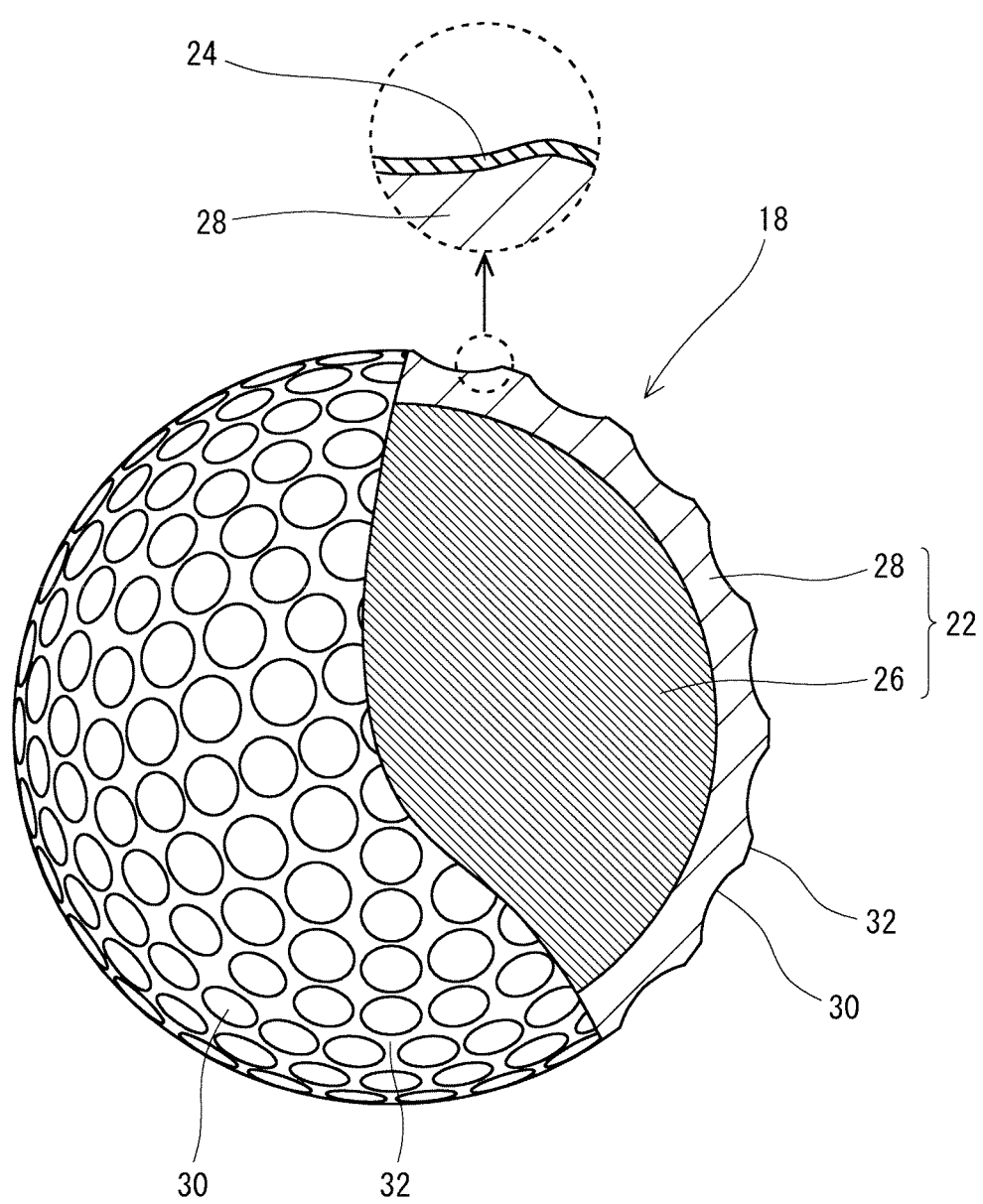
FIG. 2 is a partially cutaway cross-sectional view of a golf ball according to another embodiment of the present invention.

A golf ball 20 shown in FIG. 2 includes a main body 22 and a paint layer 24 positioned outside the main body 22. The main body 22 includes a spherical core 26 and a cover 28 positioned outside the core 26. The golf ball 20 has a so-called two-piece structure. The golf ball 20 has a plurality of dimples 30 on the surface thereof. Of the surface of the golf ball 20, a part other than the dimples 30 is a land 32. The golf ball 20 may include a mark layer. The mark layer may be positioned between the cover 28 and the paint layer 24, or may be positioned outside the paint layer 24.

The golf ball 20 preferably has a diameter of not less than 40 mm and not greater than 45 mm. From the viewpoint of conformity to the rules established by the United States Golf Association (USGA), the diameter is particularly preferably not less than 42.67 mm. In light of suppression of air resistance, the diameter is more preferably not greater than 44 mm and particularly preferably not greater than 42.80 mm. The golf ball 20 preferably has a weight of not less than 40 g and not greater than 50 g. In light of attainment of great inertia, the weight is more preferably not less than 44 g and particularly preferably not less than 45.00 g. From the viewpoint of conformity to the rules established by the USGA, the weight is particularly preferably not greater than 45.93 g.

The core 26 is formed by crosslinking a rubber composition. For the core 26, a rubber composition that is the same as the rubber composition of the core 8 shown in FIG. 1 can be used.

The core 26 has a diameter of preferably not less than 30.0 mm and particularly preferably not less than 38.0 mm. The diameter of the core 26 is preferably not greater than 42.0 mm and particularly preferably not greater than 41.5 mm. The core 26 may include two or more layers. The core 26 may have a rib on the surface thereof. The core 26 may be hollow.

The cover 28 is formed from a resin composition. For the cover 28, a resin composition that is the same as the resin composition of the mid layer 10 shown in FIG. 1 can be used. A preferable base polymer of the resin composition is an ionomer resin.

Instead of an ionomer resin or together with an ionomer resin, the resin composition of the cover 28 may include another polymer. Examples of the other polymer include polystyrenes, polyamides, polyesters, polyolefins, and polyurethanes. The resin composition may include two or more polymers.

The cover 28 preferably has a hardness Hc of not less than 50 and not greater than 80. The cover 28 having a hardness Hc of not less than 50 has excellent resilience performance. From this viewpoint, the hardness Hc is more preferably not less than 52 and particularly preferably not less than 54. The golf ball 20 including the cover 28 having a hardness Hc of not greater than 80 has excellent feel at impact and excellent spin performance. From this viewpoint, the hardness Hc is more preferably not greater than 78 and particularly preferably not greater than 76.

The hardness Hc of the cover 28 is measured according to the standards of "ASTM-D 2240-68". The hardness Hc is measured with a Shore D type hardness scale mounted to an automated hardness meter (trade name "digi test II" manufactured by Heinrich Bareiss Prüfgerätebau GmbH). For the measurement, a sheet that is formed by hot press, is formed from the same material as that of the cover 28, and has a thickness of about 2 mm is used. Prior to the measurement, a sheet is kept at 23° C. for two weeks. At the measurement, three sheets are stacked.

In light of durability, the cover 28 has a thickness Tc of preferably not less than 0.5 mm, more preferably not less than 0.8 mm, and particularly preferably not less than 1.0 mm. In light of feel at impact, the thickness Tc is preferably not greater than 3.0 mm, more preferably not greater than 2.7 mm, and particularly preferably not greater than 2.5 mm. The thickness Tc is measured at a position immediately below the land 32.

The paint layer 24 is laminated on the cover 28. The paint layer 24 is formed from a resin composition. Examples of the base material of the resin composition include polyurethanes, epoxy resins, acrylic resins, polyvinyl acetate resins, and polyesters. Particularly preferable base resins are polyurethanes. Polyurethanes can contribute to the spin performance of the golf ball 20. For the paint layer 24, a resin composition that is the same as the resin composition of the paint layer 6 shown in FIG. 1 can be used.

The paint layer 24 can be formed by applying the paint onto the surface of the main body 22. The paint may be applied in an overlapped manner. In the case of application in an overlapped manner, the paint applied earlier and the paint applied later may be of the same type or may be of different types.

The paint layer 24 preferably has a thickness Tp of not less than 5 µm and not greater than 50 µm. The paint layer 24 having a thickness Tp of not less than 5 µm can contribute to spin performance. From this viewpoint, the thickness Tp is more preferably not less than 6 µm and particularly preferably not less than 7 µm. The paint layer 24 having a thickness Tp of not greater than 50 µm has excellent durability. From this viewpoint, the thickness Tp is more preferably not greater than 40 µm and particularly preferably not greater than 30 µm. In the case where the paint is applied in an overlapped manner, the total thickness of a plurality of layers only needs to fall within the above range.

The paint layer 24 preferably has an indentation depth of not less than 300 nm and not greater than 3000 nm. The paint layer 24 having an indentation depth of not less than 300 nm can contribute to spin performance. From this viewpoint, the indentation depth is more preferably not less than 400 nm and particularly preferably not less than 450 nm. The paint layer 24 having an indentation depth of not greater than 3000 nm has excellent stain resistance. From this viewpoint, the indentation depth is more preferably not greater than 2800 nm and particularly preferably not greater than 2500 nm.

[Preferable Combination of Hardness of Cover and Indentation Depth]

A combination of a cover having a hardness Hc of not less than 20 and not greater than 50 and a paint layer having an indentation depth of not less than 400 nm and not greater than 3000 nm is preferable. A combination of a cover having a hardness Hc of not less than 50 and not greater than 80 and a paint layer having an indentation depth of not less than 300 nm and not greater than 2500 nm is also preferable.

EXAMPLES

Example 1

A rubber composition was obtained by kneading 100 parts by weight of a high-cis polybutadiene (trade name "BR-730", manufactured by JSR Corporation), 23.5 parts by weight of zinc diacrylate, 5 parts by weight of zinc oxide, an appropriate amount of barium sulfate, and 0.95 parts by weight of dicumyl peroxide. This rubber composition was placed into a mold including upper and lower mold halves each having a hemispherical cavity, and heated at 155° C. for 18 minutes to obtain a core with a diameter of 38.7 mm. The amount of barium sulfate was adjusted such that a core having a predetermined weight was obtained.

A resin composition was obtained by kneading 55 parts by weight of an ionomer resin (trade name "Himilan AM7329", manufactured by Du Pont-MITSUI POLYCHEMICALS Co., Ltd.), 45 parts by weight of another ionomer resin (trade name "Himilan 1555", manufactured by Du Pont-MITSUI POLYCHEMICALS Co., Ltd.), an appropriate amount of barium sulfate, and 3 parts by weight of titanium dioxide with a twin-screw kneading extruder. The core was covered with this resin composition by injection molding to form a cover with a thickness of 2.0 mm.

Polytetramethylene ether glycol (PTMG, number average molecular weight: 650) and trimethylol propane (TMP) were dissolved in a solvent (toluene and methyl ethyl ketone). The mole ratio (PTMG:TMP) was 1.8:1.0. Dibutyltin dilaurate was added to this solution as a catalyst in an amount of 0.1% by weight with respect to the entire base material. While this polyol solution was kept at 80° C., isophorone diisocyanate (IPDI) was dropped and mixed into the polyol solution. The mole ratio (NCO/OH) of this mixture solution was 0.6. After the dropping, the mixture solution was continuously agitated until isocyanate was eliminated. Thereafter, the mixture solution was cooled at normal temperature to obtain a base material that is a urethane polyol composition. The details of this base material are as follows.

Solid content: 30% by weight
Content of PTMG: 67% by weight
Hydroxyl value of solid content: 67.4 mg KOH/g
Weight average molecular weight of urethane polyol: 4867

Mixed were 30 parts by weight of an isocyanurate-modified product of hexamethylene diisocyanate (trade name "DURANATE TKA-100", manufactured by Asahi Kasei Chemicals Corporation, NCO content: 21.7% by weight), 30 parts by weight of a biuret-modified product of hexamethylene diisocyanate (trade name "DURANATE 21S-75E", manufactured by Asahi Kasei Chemicals Corporation, NCO content: 15.5% by weight), and 40 parts by weight of an isocyanurate-modified product of isophorone diisocyanate (trade name "Desmodur Z 4470", manufactured by Sumika Bayer Urethane CO., Ltd., NCO content: 11.9% by weight). A mixed solvent of methyl ethyl ketone, n-butyl acetate, and toluene was added as a solvent to this mixture to obtain a curing agent that is a polyisocyanate composition. The concentration of the polyisocyanate component in this curing agent was 60% by weight.

A paint was obtained by mixing the aforementioned base material (urethane polyol composition) and the aforementioned curing agent (polyisocyanate composition). The mixing ratio (weight ratio) of the base material and the curing agent was 6.4/1. The surface of a main body consisting of the aforementioned core and the aforementioned cover was treated with sandblast, and the paint was applied to the cover. The paint was dried at 40° C. for 24 hours to obtain a golf ball including a paint layer. The diameter of the golf ball was about 42.7 mm, and the weight of the golf ball was about 45.6 g.

Examples 2 and 3 and Comparative Examples 1 and 2

Golf balls of Examples 2 and 3 and Comparative Examples 1 and 2 were obtained in the same manner as Example 1, except the mixing ratio of the urethane polyol composition and the polyisocyanate composition was as shown in Tables 3 and 4 below.

Examples 4 and 5

Golf balls of Examples 4 and 5 were obtained in the same manner as Example 1, except the composition of the cover was as shown in Table 4 below. The composition of the cover is shown in detail in Table 2 below.

Example 6

A rubber composition was obtained by kneading 100 parts by weight of a high-cis polybutadiene (trade name "BR-730", manufactured by JSR Corporation), 30.5 parts by weight of zinc diacrylate, 10 parts by weight of zinc oxide, an appropriate amount of barium sulfate, 0.1 parts by weight of 2-thionaphthol, 0.3 parts by weight of pentabromo diphenyl disulfide, 0.7 parts by weight of dicumyl peroxide, and 2 parts by weight of benzoic acid. This rubber composition was placed into a mold including upper and lower mold halves each having a hemispherical cavity, and heated at 150° C. for 19 minutes to obtain a core with a diameter of 39.7 mm. The amount of barium sulfate was adjusted such that a core having a predetermined weight was obtained.

A resin composition was obtained by kneading 55 parts by weight of an ionomer resin (trade name "Himilan AM7329", manufactured by Du Pont-MITSUI POLYCHEMICALS Co., Ltd.), 45 parts by weight of another ionomer resin (trade name "Himilan 1555", manufactured by Du Pont-MITSUI POLYCHEMICALS Co., Ltd.), an appropriate amount of barium sulfate, and 3 parts by weight of titanium dioxide with a twin-screw kneading extruder. The core was covered with this resin composition by injection molding to form a mid layer with a thickness of 1.0 mm.

A paint composition (trade name "POLIN 750LE", manufactured by SHINTO PAINT CO., LTD.) including a two-component curing type epoxy resin as a base polymer was prepared. The base material liquid of this paint composition includes 30 parts by weight of a bisphenol A type epoxy resin and 70 parts by weight of a solvent. The curing agent liquid of this paint composition includes 40 parts by weight of a modified polyamide amine, 55 parts by weight of a solvent, and 5 parts by weight of titanium dioxide. The weight ratio of the base material liquid to the curing agent liquid is 1/1. This paint composition was applied to the surface of the mid layer with a spray gun, and kept at 23° C. for 12 hours to obtain a reinforcing layer with a thickness of 10 μm.

A resin composition was obtained by kneading 100 parts by weight of a thermoplastic polyurethane elastomer (trade name "Elastollan NY80A", manufactured by BASF Japan Ltd.), 4 parts by weight titanium dioxide, and 0.04 parts by weight of ultramarine blue with a twin-screw kneading extruder. Half shells were obtained from this resin composition by compression molding. The sphere consisting of the core, the mid layer, and the reinforcing layer was covered with two of these half shells. These half shells and the sphere were placed into a final mold that includes upper and lower mold halves each having a hemispherical cavity and having a large number of pimples on its cavity face, and a cover was obtained by compression molding. The thickness of the cover was 0.5 mm.

Polytetramethylene ether glycol (PTMG, number average molecular weight: 650) and trimethylol propane (TMP) were dissolved in a solvent (toluene and methyl ethyl ketone). The mole ratio (PTMG:TMP) was 1.8:1.0. Dibutyltin dilaurate was added to this solution as a catalyst in an amount of 0.1% by weight with respect to the entire base material. While this polyol solution was kept at 80° C., isophorone diisocyanate (IPDI) was dropped and mixed into the polyol solution. The mole ratio (NCO/OH) of this mixture solution was 0.6. After the dropping, the mixture solution was continuously agitated until isocyanate was eliminated. Thereafter, the mixture solution was cooled at normal temperature to obtain a base material that is a urethane polyol composition. The details of this composition are as follows.

Solid content: 30% by weight
Content of PTMG: 67% by weight
Hydroxyl value of solid content: 67.4 mg KOH/g
Weight average molecular weight of urethane polyol: 4867

Mixed were 30 parts by weight of an isocyanurate-modified product of hexamethylene diisocyanate (trade name "DURANATE TKA-100", manufactured by Asahi Kasei Chemicals Corporation, NCO content: 21.7% by weight), 30 parts by weight of a biuret-modified product of hexamethylene diisocyanate (trade name "DURANATE 21S-75E", manufactured by Asahi Kasei Chemicals Corporation, NCO content: 15.5% by weight), and 40 parts by weight of an isocyanurate-modified product of isophorone diisocyanate (trade name "Desmodur Z 4470", manufactured by Sumika Bayer Urethane CO., Ltd., NCO content: 11.9% by weight). A mixed solvent of methyl ethyl ketone, n-butyl acetate, and toluene was added as a solvent to this mixture to obtain a polyisocyanate composition that is a curing agent. The concentration of the polyisocyanate component in this composition was 60% by weight.

A paint was obtained by mixing the aforementioned base material (urethane polyol composition) and the aforementioned curing agent (polyisocyanate composition). The mixing ratio (weight ratio) of the base material and the curing agent on the solid content basis was 6.4/1. The surface of a main body consisting of the aforementioned core, the aforementioned mid layer, the aforementioned reinforcing layer, and the aforementioned cover was treated with sandblast, and the paint was applied to the cover. The paint was dried at 40° C. for 24 hours to obtain a golf ball including a paint layer. The diameter of the golf ball was about 42.7 mm, and the weight of the golf ball was about 45.6 g.

Examples 7 and 8 and Comparative Examples 3 and 4

Golf balls of Examples 7 and 8 and Comparative Examples 3 and 4 were obtained in the same manner as Example 6, except the mixing ratio of the urethane polyol composition and the polyisocyanate composition was as shown in Tables 5 and 6 below.

Example 9

A golf ball of Example 9 was obtained in the same manner as Example 6, except the composition of the cover was as shown in Table 6 below. The composition of the cover is shown in detail in Table 2 below.

[Amount of Compressive Deformation]

The amount of compressive deformation of a golf ball was measured with a YAMADA type compression tester. In the tester, the golf ball was placed on a hard plate made of metal. Next, a cylinder made of metal gradually descended toward the golf ball. The golf ball, squeezed between the bottom face of the cylinder and the hard plate, became deformed. A migration distance of the cylinder, starting from the state in which an initial load of 98 N was applied to the golf ball up to the state in which a final load of 1274 N was applied thereto, was measured. A moving speed of the cylinder until the initial load was applied was 0.83 mm/s. A moving speed of the cylinder after the initial load was applied until the final load was applied was 1.67 mm/s.

[Spin Rate]

A sand wedge was attached to a swing machine manufactured by Golf Laboratories, Inc. A golf ball was hit under a condition of a head speed of 16 m/sec, and the rate of backspin was measured. The average value of data obtained by 10 measurements is shown in Tables 3 to 6 below.

[Feel at Impact]

Thirty golf players hit golf balls with wedges and were asked about feel at impact. The evaluation was categorized as follows on the basis of the number of golf players who answered, "the feel at impact was good".

A: 25 persons or more
B: 20 to 24 persons
C: 15 to 19 persons
D: 14 persons or less The results are shown in Tables 3 to 6 below.

[Stain Resistance]

The color tone (L, a, b) of the surface of a golf ball was measured with a color difference meter ("CM3500D" manufactured by KONICA MINOLTA, INC.). An ethanol solution including 6% by weight of iodine and 4% by weight of potassium iodide (that is, iodine tincture) was prepared. The iodine tincture was diluted with water to 40-fold. The golf ball was immersed in the diluted solution for 30 seconds. The diluted solution adhering to the surface of the golf ball taken out from the diluted solution was wiped off. The color tone of the golf ball was measured again. A color difference ΔE was calculated on the basis of the following mathematical formula.

$$\Delta E = (\Delta L^2 + \Delta a^2 + \Delta b^2)^{1/2}$$

The evaluation was categorized as follows on the basis of the color difference ΔE.

A: ΔE is equal to or less than 15.
B: ΔE exceeds 15 and is equal to or less than 20.
C: ΔE exceeds 20 and is equal to or less than 25.
D: ΔE exceeds 25

The results are shown in Tables 3 to 6 below.

TABLE 1

Composition of Core (parts by weight)

|  | I | II |
|---|---|---|
| Polybutadiene rubber | 100 | 100 |
| Zinc diacrylate | 23.5 | 30.5 |
| Zinc oxide | 5 | 10 |
| Barium sulfate | * | * |
| 2-thionaphthol | — | 0.1 |
| Pentabromo diphenyl disulfide | — | 0.3 |
| Diphenyl disulfide | — | — |
| Dicumyl peroxide | 0.95 | 0.7 |
| Benzoic acid | — | 2 |
| Crosslinking Temp. (° C.) | 155 | 150 |
| Crosslinking time (min) | 18 | 19 |
| Compressive deformation (mm) | 3.5 | 3.3 |
| Central hardness Ho (ShoreC) | 64 | 53 |
| Surface hardness Hs (ShoreC) | 80 | 80 |
| Hs − Ho | 16 | 27 |

* Appropriate amount

TABLE 2

Compositions of Mid Layer and Cover (parts by weight)

|  | a | b | C | d | e |
|---|---|---|---|---|---|
| Surlyn 8150 | — | — | 32.5 | — | — |
| Surlyn 9150 | — | — | 32.5 | — | — |
| Polyamide 6 | — | — | 35 | — | — |
| Himilan AM7337 | 26 | — | — | — | — |
| Himilan AM7329 | 26 | 55 | — | — | — |
| Himilan 1555 | — | 45 | — | — | — |
| RABALON T3221C | 48 | — | — | — | — |
| Elastollan NY80A | — | — | — | 100 | — |
| Elastollan NY97A | — | — | — | — | 100 |
| Barium sulfate | * | * | * | — | — |
| Titanium dioxide | 6 | 3 | 4 | 4 | 4 |
| Ultramarine blue | — | — | — | 0.04 | 0.04 |
| Hardness (ShoreD) | 35 | 62 | 72 | 27 | 47 |

* Appropriate amount

TABLE 3

Results of Evaluation

|  |  | Comp. Ex. 1 | Ex. 2 | Ex. 1 | Ex. 3 |
|---|---|---|---|---|---|
| Core | Composition | I | I | I | I |
|  | Diameter (mm) | 38.7 | 38.7 | 38.7 | 38.7 |
|  | Ho (Shore C) | 64 | 64 | 64 | 64 |
|  | Hs (Shore C) | 80 | 80 | 80 | 80 |
|  | Hs − Ho | 16 | 16 | 16 | 16 |
| Mid layer | Composition | — | — | — | — |
|  | Hardness (Shore D) | — | — | — | — |
|  | Thickness (mm) | — | — | — | — |
| Cover | Composition | b | b | b | b |
|  | Hardness (Shore D) | 62 | 62 | 62 | 62 |
|  | Thickness (mm) | 2.0 | 2.0 | 2.0 | 2.0 |
| Paint layer | Mixing ratio | 2.6/1 | 3.06/1 | 6.4/1 | 6.8/1 |
|  | Indentation depth (nm) | 290 | 390 | 1250 | 1500 |
|  | Thickness (μm) | 10 | 10 | 10 | 10 |
| Compressive deformation (mm) |  | 2.8 | 2.8 | 2.8 | 2.8 |
| Spin rate (rpm) |  | 3650 | 3800 | 3950 | 4000 |
| Feel at impact |  | C | B | A | A |
| Stain resistance |  | A | A | B | B |

TABLE 4

Results of Evaluation

|  |  | Comp. Ex. 2 | Ex. 4 | Ex. 5 |
|---|---|---|---|---|
| Core | Composition | I | I | I |
|  | Diameter (mm) | 38.7 | 38.7 | 38.7 |
|  | Ho (Shore C) | 64 | 64 | 64 |
|  | Hs (Shore C) | 80 | 80 | 80 |
|  | Hs − Ho | 16 | 16 | 16 |
| Mid layer | Composition | — | — | — |
|  | Hardness (Shore D) | — | — | — |
|  | Thickness (mm) | — | — | — |
| Cover | Composition | b | a | c |
|  | Hardness (Shore D) | 62 | 35 | 72 |
|  | Thickness (mm) | 2.0 | 2.0 | 2.0 |
| Paint layer | Mixing ratio | 20/1 | 6.4/1 | 6.4/1 |
|  | Indentation depth (nm) | 3400 | 1250 | 1250 |
|  | Thickness (μm) | 10 | 10 | 10 |
| Compressive deformation (mm) |  | 2.8 | 2.9 | 2.7 |
| Spin rate (rpm) |  | 4200 | 4100 | 3600 |
| Feel at impact |  | A | A | B |
| Stain resistance |  | D | B | B |

TABLE 5

Results of Evaluation

|  |  | Comp. Ex. 3 | Ex. 7 | Ex. 6 |
|---|---|---|---|---|
| Core | Composition | II | II | II |
|  | Diameter (mm) | 39.7 | 39.7 | 39.7 |
|  | Ho (Shore C) | 53 | 53 | 53 |
|  | Hs (Shore C) | 80 | 80 | 80 |
|  | Hs − Ho | 27 | 27 | 27 |
| Mid layer | Composition | b | b | b |
|  | Hardness (Shore D) | 62 | 62 | 62 |
|  | Thickness (mm) | 1.0 | 1.0 | 1.0 |

TABLE 5-continued

Results of Evaluation

|  |  | Comp. Ex. 3 | Ex. 7 | Ex. 6 |
|---|---|---|---|---|
| Cover | Composition | d | d | d |
|  | Hardness (Shore D) | 27 | 27 | 27 |
|  | Thickness (mm) | 0.5 | 0.5 | 0.5 |
| Paint layer | Mixing ratio | 2.6/1 | 3.06/1 | 6.4/1 |
|  | Indentation depth (nm) | 290 | 390 | 1250 |
|  | Thickness (μm) | 10 | 10 | 10 |
| Compressive deformation (mm) |  | 2.9 | 2.9 | 2.9 |
| Spin rate (rpm) |  | 4300 | 4450 | 4600 |
| Feel at impact |  | C | B | A |
| Stain resistance |  | A | A | B |

TABLE 6

Results of Evaluation

|  |  | Ex. 8 | Comp. Ex. 4 | Ex. 9 |
|---|---|---|---|---|
| Core | Composition | II | II | II |
|  | Diameter (mm) | 39.7 | 39.7 | 39.7 |
|  | Ho (Shore C) | 53 | 53 | 53 |
|  | Hs (Shore C) | 80 | 80 | 80 |
|  | Hs − Ho | 27 | 27 | 27 |
| Mid layer | Composition | b | b | b |
|  | Hardness (Shore D) | 62 | 62 | 62 |
|  | Thickness (mm) | 1.0 | 1.0 | 1.0 |
| Cover | Composition | d | d | e |
|  | Hardness (Shore D) | 27 | 27 | 47 |
|  | Thickness (mm) | 0.5 | 0.5 | 0.5 |
| Paint layer | Mixing ratio | 6.8/1 | 20/1 | 6.4/1 |
|  | Indentation depth (nm) | 1500 | 3400 | 1250 |
|  | Thickness (μm) | 10 | 10 | 10 |
| Compressive deformation (mm) |  | 2.9 | 2.9 | 2.9 |
| Spin rate (rpm) |  | 4650 | 4800 | 4200 |
| Feel at impact |  | A | A | B |
| Stain resistance |  | B | D | B |

As shown in Tables 3 to 6, the golf ball of each Example is excellent in various performance characteristics. From the results of evaluation, advantages of the present invention are clear.

The paint layer described above is applicable to a one-piece ball, a four-piece ball, a five-piece ball, a six-piece ball, a thread-wound ball, and the like in addition to a two-piece ball and a three-piece ball. The golf ball according to the present invention is suitable for, for example, playing golf on golf courses and practicing at driving ranges. The above descriptions are merely illustrative examples, and various modifications can be made without departing from the principles of the present invention.

What is claimed is:

1. A golf ball comprising a main body and a paint layer positioned outside the main body, wherein
    the paint layer is formed from a polyurethane paint which contains a polyol composition which contains a urethane polyol,
    the urethane polyol is formed from a polyisocyanate component and a polyether diol component which has a number average molecular weight of not less than 550 and not greater than 650, and
    when the paint layer is pressed in a direction perpendicular to a cross-section along a plane passing through a central point of the golf ball, the measured paint layer indentation depth is not less than 300 nm and not greater than 1500 nm.

2. The golf ball according to claim 1, wherein the measured indentation depth is not less than 400 nm and not greater than 1500 nm.

3. The golf ball according to claim 1, wherein the paint layer has a thickness of not less than 5 μm and not greater than 50 μm.

4. The golf ball according to claim 1, wherein
    the main body includes a core and a cover positioned outside the core,
    the paint layer is laminated on the cover,
    the cover has a Shore D hardness of not less than 20 and not greater than 50, and
    the measured indentation depth is not less than 400 nm and not greater than 1500 nm.

5. The golf ball according to claim 1, wherein
    the main body includes a core and a cover positioned outside the core,
    the paint layer is laminated on the cover,
    the cover has a Shore D hardness of not less than 50 and not greater than 80, and
    the measured indentation depth is not less than 300 nm and not greater than 1500 nm.

6. The golf ball according to claim 1, wherein the content of the polyether diol in the urethane polyol is not less than 60% by weight.

7. The golf ball according to claim 1, wherein
    the paint layer is formed from a polyurethane paint which contains a polyisocyanate composition which contains a triisocyanate compound, and
    the proportion of triisocyanate compound to all polyisocyanate components in the polyisocyanate composition is not less than 50% by weight.

8. The golf ball according to claim 1, wherein
    the main body includes a core, a mid layer positioned outside the core, and a cover positioned outside the mid layer, and
    the mid layer has a Shore D hardness of not less than 40 and not greater than 80.

9. The golf ball according to claim 1, wherein
    the main body includes a core, a mid layer positioned outside the core, and a cover positioned outside the mid layer, and
    the mid layer has a thickness of not less than 0.2 mm and not greater than 2.5 mm.

10. The golf ball according to claim 1, wherein
    the main body includes a core, a mid layer positioned outside the core, and a cover positioned outside the mid layer, and
    the mid layer has a specific gravity of not less than 0.90 and not greater than 1.10.

11. The golf ball according to claim 4, wherein the cover has a thickness of not less than 0.1 mm and not greater than 2.0 mm.

12. The golf ball according to claim 5, wherein the cover has a thickness of not less than 0.5 mm and not greater than 3.0 mm.

* * * * *